United States Patent
Terrisse

(10) Patent No.: US 8,470,034 B2
(45) Date of Patent: Jun. 25, 2013

(54) HYDROPHOBIC ACRYLIC POLYMER MATERIAL FOR AN INTRAOCULAR LENS HAVING ENHANCED FLEXIBILITY DUE TO THE USE OF A TRANSFER AGENT

(75) Inventor: Jean Terrisse, Strasbourg (FR)

(73) Assignee: Acrylian, Strasbourg (FR)

( * ) Notice: Subject to any disclaimer, the term of this patent is extended or adjusted under 35 U.S.C. 154(b) by 0 days.

(21) Appl. No.: 12/736,973

(22) PCT Filed: Apr. 29, 2009

(86) PCT No.: PCT/FR2009/000505
§ 371 (c)(1),
(2), (4) Date: Nov. 29, 2010

(87) PCT Pub. No.: WO2009/138591
PCT Pub. Date: Nov. 19, 2009

(65) Prior Publication Data
US 2011/0245442 A1    Oct. 6, 2011

(30) Foreign Application Priority Data

Apr. 30, 2008 (FR) ...................................... 08 02427

(51) Int. Cl.
*A61F 2/16* (2006.01)
*C08F 20/28* (2006.01)

(52) U.S. Cl.
USPC .......... 623/6.56; 526/206; 526/222; 526/224; 526/227; 526/228; 526/232.5; 526/323.2; 526/325; 526/328.5; 526/332; 526/333; 528/271; 623/6.11

(58) Field of Classification Search
USPC .............. 526/206, 222, 224, 227, 228, 232.5, 526/323.2, 325, 328.5, 332, 333; 528/271; 623/6.11, 6.56
See application file for complete search history.

(56) References Cited

U.S. PATENT DOCUMENTS

| 4,904,421 | A  | * | 2/1990  | Ando et al. ..................... 264/2.6 |
| 6,326,448 | B1 | * | 12/2001 | Ojio et al. ...................... 526/259 |
| 6,465,588 | B1 | * | 10/2002 | Li .................................. 526/258 |
| 6,713,584 | B1 | * | 3/2004  | Chisholm et al. .......... 526/329.7 |

FOREIGN PATENT DOCUMENTS

| WO | 01/05578 | 1/2001 |
| WO | 01/18079 | 3/2001 |

* cited by examiner

*Primary Examiner* — Richard A Huhn
(74) *Attorney, Agent, or Firm* — Heslin Rothenberg Farley & Mesiti P.C.

(57) ABSTRACT

The material of the invention is obtained by radical polymerization from a mixture of acrylic and/or methacrylic monomers. The mixture further contains at least one transfer agent, preferably from the thiol family, that substantially enhances the flexibility of the polymer material thus obtained, and reduces the tackiness thereof. The polymer material thus obtained is intended for making ophthalmologic implants, and more particularly, intraocular lenses.

16 Claims, 2 Drawing Sheets ize of
HYDROPHOBIC ACRYLIC POLYMER MATERIAL FOR AN INTRAOCULAR LENS HAVING ENHANCED FLEXIBILITY DUE TO THE USE OF A TRANSFER AGENT The present invention relates to a novel hydrophobic acrylic polymer material having enhanced flexibility due to the addition of a transfer agent, this material being particularly suitable for production of intraocular lenses.

The invention also relates to a method for manufacturing such a polymer material as well as to intraocular lenses produced from this novel polymer material.

Intraocular lenses are ophthalmological implants or prostheses placed surgically in the eye of patients suffering, for example, from cataracts, to replace their failing crystalline lens.

During this surgical procedure, the surgeon begins by removing the diseased natural crystalline lens from the patient. To do so, he makes a small incision in the patient's cornea and inserts through it an instrument known as a phacoemulsifier, the end of which punctures the anterior wall of the crystalline lens capsule and passes through this wall.

This instrument makes it possible to fragment the crystalline lens by emission of ultrasonic vibrations, to inject physiological serum for dissolving the fragments and simultaneously to aspire the solution containing the fragments of crystalline lens.

The surgeon, after having injected a lubricant of the hyaluronate gel type therein, places, in the crystalline lens capsule, the intraocular lens which is to replace the crystalline lens.

This lens is traditionally composed of a corrective optical part, whose correction varies from 10 to 30 diopters depending on the case. This optical part has substantially the form of a disk and exhibits a generally asymmetric biconvex cross section. It must be positioned centrally relative to the optical axis of the eye.

From this central optical part there extend lateral prolongations known as haptics, generally two or four in number and which may have varied shapes. The role of these haptics is to stretch the walls of the crystalline lens capsule and to assure correct positioning of the lens relative to the optical axis of the eye.

Via the incision in the cornea that was previously used to remove the crystalline lens, the intraocular lens is implanted in the patient's eye by means of an injector equipped with an injection tube, whose outside diameter is smaller than that of the incision and whose open end is introduced through this incision.

To ensure that the procedure causes as little trauma as possible for the patient, and to avoid the development of post-operative astigmatism, the incision made in the cornea must be as small as possible.

The width of these incisions has been considerably reduced in the course of recent years. Incisions are now being made with a length on the order of 2.5 mm, and it is hoped that a width of 2.2 mm will soon be attained, and even 2 mm in the future.

The intraocular lens, which has clearly larger diameter, must therefore be placed beforehand in a folded insertion configuration that permits it to pass through this incision of very short length.

For this purpose, the lens is placed together with an aqueous solution of hyaluronic acid, for example, in the charging chamber of an injection cartridge, which upon being closed causes the lens to curl up on itself. Once the injection cartridge is mounted in the injector, a piston pushes the rear end of the lens into the injection tube of the injector, compressing it, as well as its haptics even more, and causing it to be expelled beyond the injector into the crystalline lens capsule of the patient's eye.

Once released into the crystalline lens capsule, the intraocular lens must be deployed rapidly so that it can be positioned correctly and be capable of fulfilling its function of optical correction in satisfactory manner.

To ensure that the lens can be placed without problems, the material must be sufficiently flexible that it can be folded and curled up on itself. It must resist stretching and the pushing pressure without being ruptured and without breaking the injection tube, so that it can pass through an ejection orifice of extremely reduced diameter, on the order of 1.5 mm or even smaller.

Finally, once it is in the patient's eye, the intraocular lens must be capable of deploying completely on its own, without remaining stuck to itself, and in a relatively short time, so that it becomes positioned correctly in the crystalline lens capsule and recovers its optical characteristics.

In the prior art, attempts have been made to reduce the size of intraocular lenses in such a way that they can be introduced more easily via a progressively smaller incision. To preserve the optical properties of these lenses, it was necessary to find materials of progressively higher refractive indices. However, problems of dazzle were then encountered due to multiple light reflections between the retina and the lens.

Another approach was to use a more deformable material to produce lenses of the same size and constant index.

The plastic materials used for this purpose in the prior art may be divided into two large categories: the plastic materials known as "hydrophilic" and those known as "hydrophobic".

The "hydrophilic" plastic materials are the more deformable. Their size and flexibility depend on the amount of water absorbed. They are hard and compact in the absence of water, permitting them to be machined easily at room temperature. When they are hydrated, they dilate and become soft and flexible, permitting them to be implanted in the eye.

However, these "hydrophilic" lenses, which contain almost 25% water at the temperature of the eye, are in equilibrium with the aqueous humor of the eye in which they are implanted. But because it is difficult to free the hydrophilic lenses entirely of their synthesis impurities and manufacturing residues, products originating from the lens may diffuse into the eye and cause inflammations and in certain cases even serious disorders.

The plastic materials of the second category, known as "hydrophobic", exhibit specific characteristics that do not depend on the amount of water absorbed. They may be easily purified and freed of water-insoluble residual products during manufacture.

Examples are acrylic or silicone-base polymers.

The flexibility of these materials depends on their temperature. They have a glass transition temperature (Tg) below which they are hard and may be machined and above which they become flexible, deformable and elastic.

To produce intraocular lenses, it is necessary to choose a material having a sufficiently low glass transition temperature that the resulting lens is flexible enough to be curled up and stretched out at the temperature of an operating room, or in other words approximately 18 to 20° C.

The invention relates to these plastic materials known as "hydrophobic" and more particularly to the acrylic polymers.

The well known problem of these hydrophobic materials is that, as their flexibility and deformability increase, they become stickier.

Because of this fact, these intraocular lenses may have difficulty in deploying correctly when they are implanted in the patient's eye. In particular, the haptics very often remain stuck to the optical part of the lens.

This defect occurs regardless of the geometric form of the haptics. It is aggravated by the fact that, in order to reduce the overall space requirement of the lenses so that they can be passed through an incision of minimum size, the thickness of the median zone of the lens, which is optically inactive, is made as small as possible, as is that of the haptics prolonging it.

Because the thickness is reduced in the zone of attachment of the haptics, forming a hinge, the spring force of the material, which normally acts to unfold the haptics, is clearly diminished and is no longer sufficient to overcome the force of adherence of the sticky material and to detach the haptics from the optical part of the lens.

The surgeon must then attempt to detach them manually by means of a small tool, which he passes through the incision in place of the injector. This operation, which is risky and particularly delicate, most often ends in failure.

To solve this technical problem, it has been proposed in the prior art that the surface of the lenses be treated, after their manufacture, to make them more slippery and less sticky. As an example, Patent Application WO 94/25510, for example, proposes to expose their surface to a plasma for this purpose.

The invention offers a different solution to this problem by providing a novel flexible hydrophobic acrylic polymer material, intended for the production of ophthalmological implants, and more particularly of intraocular lenses.

This material is obtained by radical polymerization starting from a mixture of acrylic monomers or a mixture of acrylic and methacrylic monomers. According to the invention, this mixture additionally comprises at least one transfer agent, especially a thiol containing preferably four to seventeen carbon atoms, or a halogenated product, preferably chlorinated.

Intraocular lenses to be implanted surgically in the crystalline lens capsule, replacing the natural crystalline lens, may be produced advantageously from such an acrylic polymer material.

The invention also provides a method for manufacturing such an acrylic polymer material by radical polymerization starting from a mixture of acrylic monomers or a mixture of acrylic and methacrylic monomers, wherein a transfer agent is added to the monomers before their polymerization.

To start the process of polymerization of this material, it is possible to add one or more initiator compounds to the mixture.

According to a preferred embodiment of the invention, the mixture of monomers may advantageously contain at least:
  an arylalkoxy acrylate or an arylalkoxy methacrylate;
  an alkyl acrylate;
  a hydroxylated acrylate;
  a hydroxylated methacrylate;
  a diol diacrylate; and
  a diol dimethacrylate.

By virtue of the action of the transfer agent, the acrylic polymer material according to the invention is surprisingly particularly flexible and deformable at room temperature and exhibits great ability to deform without rupture at the temperatures of placement and use of the lens, or in other words between 18 and 35° C. It may be easily curled up and stretched out without problem for implantation in the patient's eye.

In this way the present inventors have successfully passed, without damage, a lens made of a material according to the invention through an incision of 1.5 mm width, which corresponds to a very much smaller width than the 2.5 mm currently practiced and even much smaller than the 2 mm hoped for by the profession, and which represents considerable and surprising progress compared with the prior art.

In addition, the material according to the invention does not stick to itself in the presence of water. It may therefore be deployed easily and entirely once positioned in the patient's eye, in this way satisfactorily solving the problem of haptics remaining stuck to the optical part of intraocular lenses.

Since the spring force necessary at the hinge for unfolding the haptics is smaller, because there is less adherence, the median zone of the lens and of its haptics may be advantageously reduced to decrease the overall space requirement of the lens, without detrimental consequence for its deployment during placement.

Other characteristics and advantages of the invention will become apparent upon reading the detailed description hereinafter.

To facilitate the good understanding of the reader, this description is accompanied by way of example by the following attached drawings, wherein:

FIGS. 1 and 2 show two traditional examples of intraocular lens 1 that can be produced from an acrylic polymer material according to the invention.

These lenses 1 have a central optical part 2, substantially in the form of a disk, with a biconvex profile.

From this optical part 2 there extend lateral prolongations known as haptics 3.

Figure 1:
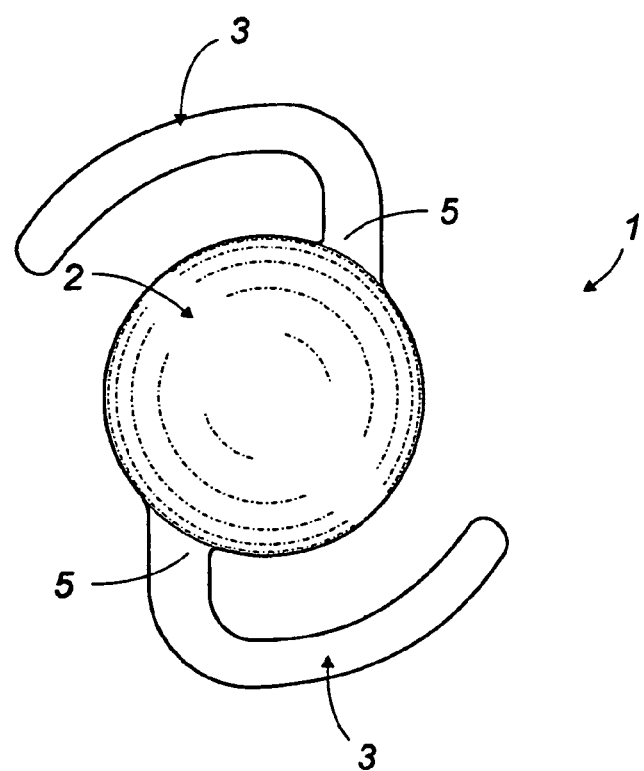
FIG. 1 is a first example of an intraocular lens that can be produced from a material according to the invention.

In FIG. 1, there are two of these haptics 3. They are disposed in diametrically opposite manner and have the form of bent arms pointing in opposite directions.

Figure 2:
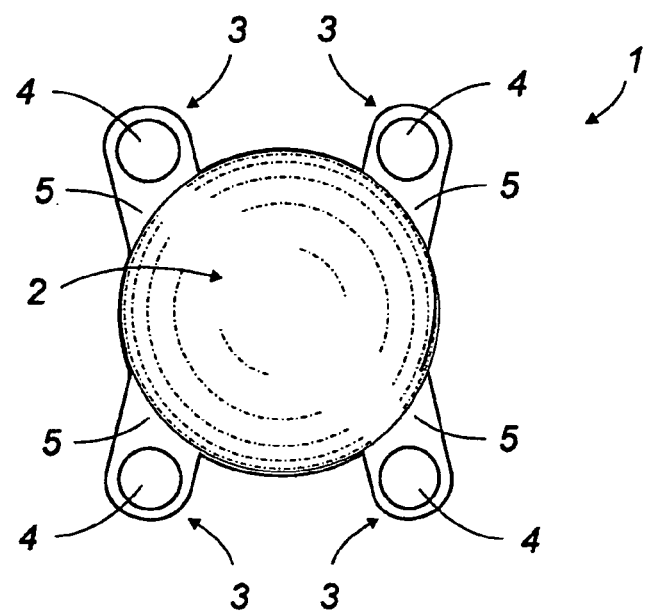
FIG. 2 is a second example of an intraocular lens that can be produced from a material according to the invention.

The lens of FIG. 2 has four haptics 3 in the form of a ring pierced by a central orifice 4. These haptics 3 are distributed regularly around the periphery of optical part 2.

In the illustrated examples, haptics 3 are made in one piece with optical part 2 of lens 1. This type of lens is known as a "monobloc lens". The material according to the invention is perfectly suitable for the production of such lenses.

Haptics 3 are connected to central optical part 2 by a junction zone 5 forming a hinge, which generates a spring effect by elastic restoration of the material to unfold the lens during its implantation into a patient's eye.

Figure 3:
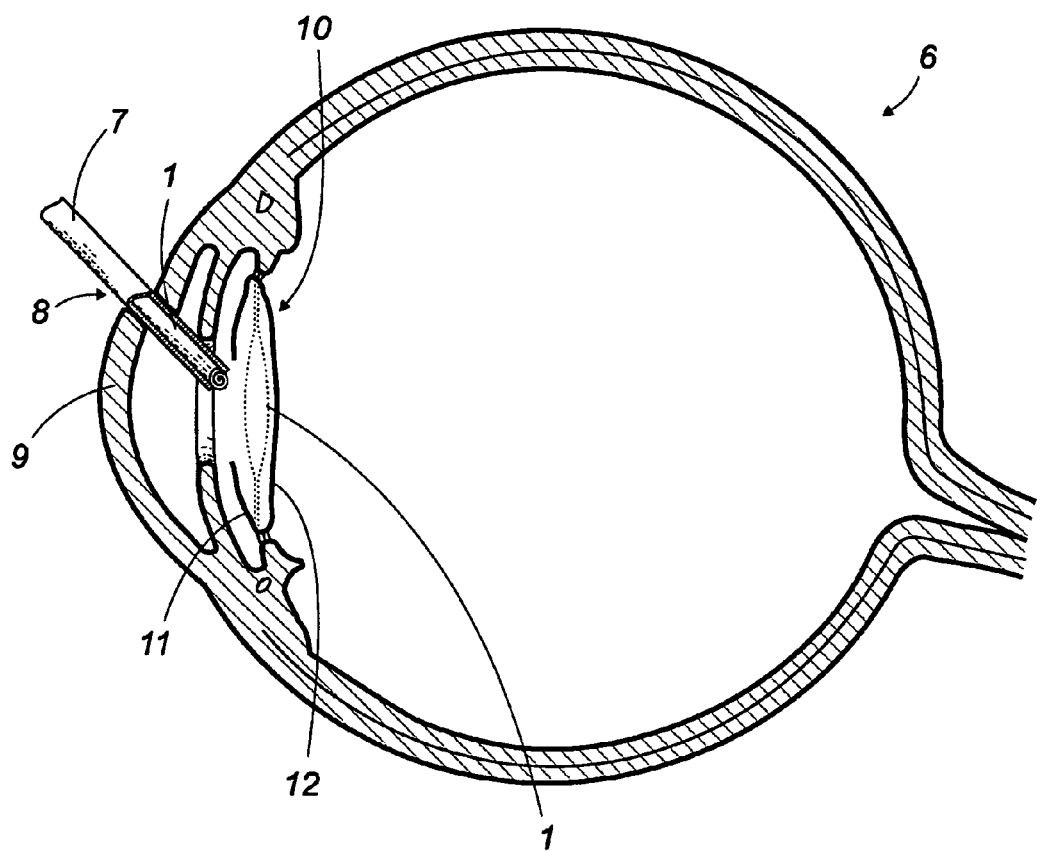
FIG. 3 is a schematic drawing illustrating the implantation, in the eye of a patient, of an intraocular lens produced from a material according to the invention.

FIG. 3 schematically illustrates the procedure for implantation of an intraocular lens 1 in eye 6 of a patient.

As explained in the introductory part, lens 1 is curled up on itself in the interior of an injector 7, whose end is introduced through a small-size incision 8 made beforehand in cornea 9 of the patient.

The end of injector 7 then penetrates into crystalline lens capsule 10, from which the crystalline lens was voided beforehand.

Intraocular lens 1 is then ejected into crystalline lens capsule 10, where it deploys and becomes positioned by virtue of its haptics 3 between anterior wall 11 and posterior wall 12 of the capsule. Intraocular lens 1 is maintained by its haptics 3 in its position of use, as illustrated by dotted lines in FIG. 3.

The material according to the invention is particularly suitable for the production of such intraocular lenses 1.

It is an acrylic polymer obtained by radical polymerization starting from a mixture of acrylic and/or methacrylic monomers, and which constitutes a cross-linked acrylic system.

According to the invention, the initial mixture of monomers additionally contains one or more transfer agent(s).

Surprisingly, the present inventors found that the addition of a small proportion of transfer agent to these cross-linked acrylic systems made it possible to reduce, simultaneously and considerably, two particularly troublesome and well known properties of these acrylic polymers: on the one hand the fragile and brittle nature of highly cross-linked polymers, which is reflected by an elongation at break inversely proportional to the degree of cross-linking, and on the other hand the sticky nature of these polymers, which increases with chain length between the cross-linking nodes and becomes particularly troublesome for poorly cross-linked systems.

These two properties act in opposite directions: As the degree of cross-linking increases, the resulting polymer becomes less sticky, but it is more fragile and breaks with a deformation limited to values between 60 and 100%.

The inventors noted that the transfer agent advantageously increases the ability of the material to deform without rupture. The addition of a transfer agent to the mixture makes it possible to have a high degree of cross-linking and therefore a resulting polymer that is scarcely sticky, while surprisingly retaining a large elongation at break.

This transfer agent stops the polymerization locally by transferring the radical from one monomer to another. The formation of the three-dimensional mesh structure is therefore interrupted locally, and in this zone there is obtained a mesh cut with a short dangling chain connected to the network but whose other end remains free. In this way the transfer agent makes it possible to obtain a looser mesh structure capable of being stretched more without rupture at a high degree of cross-linking.

The transfer agent may be a halogenated product, for example chlorinated, or more preferably a compound of the thiol family.

It is preferably a thiol containing four to seventeen carbon atoms, for example butanethiol, octanethiol or dodecanethiol, the latter two compounds being preferred because they are easier to dose and are more stable in composition.

Of course, the composition may contain several transfer agents, preferably chosen from among the compounds cited above.

Advantageously, a very small content of transfer agent is necessary to achieve this result. Thus the initial mixture preferably contains between 0.03% and 0.1% by weight of transfer agent, more preferably yet between 0.04% and 0.07% of transfer agent, 0.05% being a preferred value for butanethiol.

This transfer agent or these transfer agents has or have the function of modifying the structure of the macromolecular network in such a way that they considerably increase the deformability before rupture and slow the rate of propagation of cracks under stress.

They act on the mechanical properties of the network without modifying the chemistry. In this way they make it possible to obtain, at constant degree of cross-linking, much greater deformability of the constituted network, which is reflected by considerable slowing of the appearance and propagation of cracks, as proved by the two series of tests described below.

In order to demonstrate the action of the transfer agent, the tests were carried out on several polymer materials produced with or without transfer agent and with a transfer agent used in variable proportion.

In each series, three different polymers were obtained from the same initial mixture of monomers and initiator and with a variable proportion of transfer agent. The proportions are expressed in percent by weight of monomers.

Polymers of Series A: $A_0$, $A_{0.05}$ and $A_{0.08}$

| MONOMERS: | | | |
|---|---|---|---|
| phenoxyethyl acrylate | | 83% | |
| hexyl acrylate | | 10% | |
| hydroxyethyl methacrylate | | 5.5% | |
| ethylene glycol diacrylate | | 1.5% | |
| INITIATOR COMPOUND: | | | |
| peroxide | | 0.5% | |
| TRANSFER AGENT: | $A_0$ | $A_{0.05}$ | $A_{0.08}$ |
| butanethiol | 0% | 0.05% | 0.08% |

Polymers of Series B: $B_0$, $B_{0.04}$ and $B_{0.07}$

| MONOMERS: | | | | |
|---|---|---|---|---|
| 2-ethoxyethyl methacrylate | | 73% | | |
| butyl acrylate | | 17% | | |
| hydroxyethyl methacrylate | | 8% | | |
| ethylene glycol dimethacrylate | | 2% | | |
| INITIATOR COMPOUND: | | | | |
| peroxide | | 0.8% | | |
| TRANSFER AGENT: | Polymer: | $B_0$ | $B_{0.04}$ | $B_{0.07}$ |
| butanethiol | | 0% | 0.04% | 0.07% |

Polymers of Series C: $C_0$, $C_{0.05}$ and $C_{0.1}$

| MONOMERS: | | | | |
|---|---|---|---|---|
| 2-ethoxyethyl methacrylate | | 61.5% | | |
| lauryl acrylate | | 37% | | |
| ethylene glycol dimethacrylate | | 1.5% | | |
| INITIATOR COMPOUND: | | | | |
| peroxide | | 0.5% | | |
| TRANSFER AGENT: | Polymer: | $C_0$ | $C_{0.05}$ | $C_{0.1}$ |
| butanethiol | | 0% | 0.05% | 0.1% |

Polymers of Series D: $D_0$, $D_{0.04}$ and $D_{0.08}$

| MONOMERS: | | | | |
|---|---|---|---|---|
| phenoxyethyl methacrylate | | 73% | | |
| hydroxyethyl methacrylate | | 11% | | |
| butyl acrylate | | 15% | | |
| ethylene glycol dimethacrylate | | 1% | | |
| INITIATOR COMPOUND: | | | | |
| peroxide | | 0.5% | | |
| TRANSFER AGENT: | Polymer: | $D_0$ | $D_{0.04}$ | $D_{0.08}$ |
| butanethiol | | 0% | 0.04% | 0.08% |

Using the different materials tested, sheets of 3 mm thickness were formed and disks of 16 mm diameter were cut out from them. For each of the materials tested, a lot of approximately ten samples was prepared, the measurements were performed on each sample and a mean result was calculated for the lot.

The objective of the first series of tests was to compare the resistance to spontaneous cracking of these materials in case of deformation.

For this purpose, the disks were folded over on themselves by 180° along a diametral fold. The folded disks were placed between two glass plates, the whole being held in place by a clamp. These assemblies were immersed in water at 35° C. for two minutes in order to guarantee a constant and uniform experimental temperature for the different samples. The number of samples on which a crack appeared spontaneously at the fold was then counted. This number was then converted into a degree of cracking in less than two minutes for each lot of samples, this value being expressed as a percentage.

The objective of the second series of tests was to compare the speed of propagation of a crack developed in these different materials.

For this purpose, as in the foregoing, the disks were folded over on themselves by 180° along a diametral fold and placed between two glass plates, the whole being held by a clamp. On each disk, two marks were then made on the fold line, each 3 mm from one of the edges. The assemblies were then immersed in water at 35° C.

After a waiting time of two minutes, permitting the assembly to reach the experimental equilibrium temperature, propagation of a crack was then initiated by notching each sample with a scalpel on one of the edges of the fold. The propagation of the crack along the fold was observed by means of a camera. The analysis of films made it possible to measure the time necessary for the crack in each sample to propagate from the first mark to the second mark. In this way the measurements made from one mark to the other are independent of edge effects. The measured propagation time was then converted into crack propagation speed, expressed in millimeters per second.

In order to permit a comparative analysis, the results of these two tests for each series of polymers are grouped in the tables below:

Polymers of Series A:

|  | $A_0$ | $A_{0.05}$ | $A_{0.08}$ |
|---|---|---|---|
| Test No. 1: | | | |
| Cracking percentage in less than 2 minutes | 100% | 0% | 30% |
| Test No. 2: | | | |
| Crack propagation speed | 2 mm/s | 0.2 mm/s | 0.7 mm/s |

Polymers of Series B:

|  | $B_0$ | $B_{0.04}$ | $B_{0.07}$ |
|---|---|---|---|
| Test No. 1: | | | |
| Cracking percentage in less than 2 minutes | 100% | 0% | 0% |
| Test No. 2: | | | |
| Crack propagation speed | 3 mm/s | 0.8 mm/s | 1.2 mm/s |

Polymers of Series C:

|  | $C_0$ | $C_{0.05}$ | $C_{0.1}$ |
|---|---|---|---|
| Test No. 1: | | | |
| Cracking percentage in less than 2 minutes | 100% | 0% | 0% |
| Test No. 2: | | | |
| Crack propagation speed | 2.5 mm/s | 1.5 mm/s | 2 mm/s |

Polymers of Series D:

|  | $D_0$ | $D_{0.04}$ | $D_{0.08}$ |
|---|---|---|---|
| Test No. 1: | | | |
| Cracking percentage in less than 2 minutes | 80% | 0% | 0% |
| Test No. 2: | | | |
| Crack propagation speed | 1.3 mm/s | 0.3 mm/s | 0.8 mm/s |

It is therefore evident that the addition of a small proportion of transfer agent permits a considerable improvement in the resistance to spontaneous cracking and a large reduction of the speed of propagation of induced cracks. This result is independent of the nature of the acrylate and/or methacrylate monomers used.

According to these tests, the optimum results seem to be obtained with a butanethiol content of 0.04 to 0.05%.

By virtue of the addition of a transfer agent, it is therefore possible to increase the cross-linking of the final acrylic polymer in order to reduce its sticky nature, without making it fragile and brittle. Advantageously there is obtained an acrylic polymer material that is flexible and non-sticky, particularly well adapted to production of intraocular lenses, which may therefore be deformed and stretched out without damage in order to be inserted through very small incisions, and which then deploy without remaining stuck once placed in the patient's eye.

The addition of a transfer agent yields yet another advantage during the manufacture of intraocular lenses, in that it makes the acrylic polymer more easily machinable by preventing the cuttings formed from sticking to the lens in the course of manufacture.

In addition to monomers and the transfer agent, the initial mixture may contain a certain number of supplementary compounds of different nature.

It comprises, for example, an initiator compound which acts to start the polymerization reaction by creating active sites on the monomers. This compound makes it possible to regulate the kinetics of the polymerization reaction.

The mixture may contain several initiator compounds and preferably two initiator compounds of very different reactivity, for example one ten to twenty times as fast as the second.

The alkyl peroxides are examples of usable initiator compounds, with preferably lauroyl diperoxide, commonly referred to as lauroyl peroxide, which is highly reactive at 80° C. and is the least dangerous of this family. To it there may be added, if need be, a second more stable initiator, such as 1,1-di-tert-butylperoxycyclohexane or an equivalent with substantially the same reactivity.

This compound or these compounds is or are added to the mixture in very small proportions, the mixture comprising, for example, between 0.3 and 1% by weight of initiator compound.

The mixture may also contain, for example, one or more anti-ultraviolet agents, one or more polymerizable or non-polymerizable coloring agents or any other constituent that may be imagined by the person skilled in the art and that may have any function whatsoever compatible with the production of intraocular lenses.

The content of anti-ultraviolet and/or coloring agent(s) is preferably between 0.1 and 1% by weight.

To obtain the acrylic polymer according to the invention, a mixture of acrylic and/or methacrylic monomers additionally containing at least one transfer agent is subjected to radical polymerization.

By way of non-limitative example, there will be described below a mixture of particular monomers that makes it possible to obtain, according to the invention, a particularly advantageous polymer material. It is evident that the person skilled in the art will be able to imagine numerous other mixtures based on different acrylic and/or methacrylic monomers without going beyond the scope of the invention defined by the claims.

According to this preferred embodiment, the mixture of monomers contains at least:

an arylalkoxy acrylate or an arylalkoxy methacrylate;
an alkyl acrylate;
a hydroxylated acrylate;
a hydroxylated methacrylate;
a diol diacrylate; and
a diol dimethacrylate.

The use of an arylalkoxy acrylate or of an arylalkoxy methacrylate makes it possible to obtain a final polymer of high refractive index.

As arylalkoxy acrylate or arylalkoxy methacrylate it is possible to use a compound chosen from among 2-phenoxyethyl acrylate, 2-phenoxy-2-ethoxyethyl acrylate, 2-phenoxy-2-ethoxy-2-ethoxyethyl acrylate and its higher oligomers for the arylalkoxy acrylate and from among 2-phenoxyethyl methacrylate, 2-phenoxy-2-ethoxyethyl methacrylate, 2-phenoxy-2-ethoxy-2-ethoxyethyl methacrylate and its higher oligomers for the arylalkoxy methacrylate.

By way of a preferred example there can be cited 2-phenoxyethyl acrylate, the arylalkoxy acrylates being generally preferred to the arylalkoxy methacrylates, because they have a much lower glass transition temperature.

The initial mixture before polymerization preferably comprises between 45 and 89% by weight of arylalkoxy acrylate or arylalkoxy methacrylate. Preferably it contains between 66 and 75% by weight of arylalkoxy acrylate or arylalkoxy methacrylate, with a preferred value on the order of 74%.

At least one alkyl acrylate is added to the mixture for the purpose of lowering the glass transition temperature of the resulting polymer. For this purpose it is therefore possible to use all the alkyl acrylates which, once polymerized, have a low glass transition temperature and are not too sticky.

For practical reasons, it is preferable to limit the alkyl acrylates to those having a boiling temperature above 100° C., in order to avoid problems of bubbles.

The alkyl acrylate used preferably contains an alkyl chain having 4 to 6 carbon atoms, among which butyl acrylate may be advantageously chosen.

The initial mixture before polymerization preferably comprises between 5 and 20% by weight of alkyl acrylate, more preferably between 10 and 15%, 10% being a preferred value.

To lessen the sticky nature of the material in the presence of water. the final polymer must have a sufficient proportion of hydroxyl functions at the surface. In this way water forms a continuous film on the surface of the material, which no longer sticks to itself provided it has a surface tension higher than 40 dyne/cm.

Thus hydroxylated monomers—a hydroxylated acrylate and a hydroxylated methacrylate—are added to the mixture, increasing the surface tension and the affinity of the surface of the resulting polymer for water.

To be acceptable, these monomers must not have, in the polymerized state, a glass transition temperature that is too high, or in other words above 0° C.

The hydroxylated acrylate used is, for example, a dihydroxyalkyl or dihydroxy-ethoxyalkyl monoacrylate, wherein the alkyl chain of the glycol contains 2 to 6 carbon atoms. There may be cited, for example, hydroxyethyl acrylate, hydroxybutyl acrylate, known as butanediol acrylate, hexanediol acrylate, diethylene glycol monoacrylate and triethylene glycol monoacrylate.

The hydroxylated methacrylate used is preferably a dihydroxyalkyl or dihydroxy-ethoxyalkyl monomethacrylate, wherein the alkyl chain of the glycol contains 2 to 6 carbon atoms. It relates, for example, to hydroxyethyl methacrylate, butanediol monomethacrylate, hexanediol monomethacrylate, diethylene glycol monomethacrylate or triethylene glycol monomethacrylate.

The proportion of these hydroxylated monomers in the mixture prior to polymerization must be sufficient for the resulting material to have a suitable surface tension and to resist bleaching upon prolonged contact with water at 35° C. However, it must not be too high, so that the resulting material remains hydrophobic on the whole and does not absorb too much water, in order to avoid the specific problems of hydrophilic materials.

Advantageously, the hydroxylated acrylate and the hydroxylated methacrylate together represent preferably between 5 and 20% by weight of the mixture, and more preferably around 16 to 17% of the mixture.

Depending on the case, the proportion of these two hydroxylated monomers relative to one another may vary from 30 to 70% for the one and inversely for the other according to the desired glass transition temperature.

The mixture also contains cross-linking compounds that make it possible to obtain a three-dimensional network and not linear polymers during polymerization. To obtain such a mesh structure, difunctional in preference to trifunctional monomers are added: preferably a diol diacrylate and a diol dimethacrylate.

The use of a diacrylate and of a dimethacrylate at the same time makes it possible to obtain a homogeneous final mixture, in which all of the initial monomers are bound and do not separate into distinct phases. In fact, the initial mixture of monomers contains acrylate compounds and methacrylate compounds that do not polymerize at the same rate. The mixture of these two cross-linking agents makes it possible to cross-link all of the monomers with a homogeneous distribution of the cross-linking nodes in the resulting polymer, the degree of branching being substantially constant throughout the polymerization.

These cross-linking compounds contain ethoxy and possibly hydroxy functions, so as not to increase the glass transition temperature of the final material and at the same time maintain a hydrophilicity level that is homogeneous with the rest of the composition.

The diol diacrylate used is preferably diethylene glycol diacrylate, triethylene glycol diacrylate or an alkyldiol diacrylate whose alkyl chain contains 2 to 6 carbon atoms.

The diol dimethacrylate used may be diethylene glycol dimethacrylate or an alkyldiol dimethacrylate, wherein the alkyl chain contains 2 to 6 carbon atoms. A hydroxylated dimethacrylate such as glycerol diacrylate provides a supplementary contribution to the hydrophilicity.

The proportion of cross-linking agents must be sufficient that not too many dangling long chains rich in alkyl acrylate or in arylalkoxy acrylate remain in the final polymer, since they increase the sticky nature of the polymer.

In addition, a greater degree of cross-linking and a shorter relaxation time of the polymer mean commensurately faster deployment of the lens in the eye at constant glass transition temperature.

On the other hand, however, it might be expected that the resulting polymer becomes brittle if its degree of cross-linking is too high. Nevertheless, this phenomenon is considerably reduced by the use according to the invention of at least one transfer agent.

The proportion of diol diacrylics and of diol dimethacrylics is carefully chosen. Preferably these cross-linking compounds are added to the mixture in proportions such that the final cross-linking level, or in other words a weight between cross-linking nodes, is between 2000 gr/M and 10,000 gr/M.

Advantageously the diol diacrylate and diol dimethacrylate together represent preferably between 1 and 3% by weight of the mixture, the relative proportion between the diol diacrylate and diol dimethacrylate varying preferably from 30 to 70% of the one relative to the other and inversely.

In summarizing the considerations detailed hereinabove, it is possible to imagine a particular mixture of monomers that leads by radical polymerization to a preferred embodiment of the material according to the invention.

This mixture preferably comprises at least the following monomers: 2-phenoxyethyl acrylate, butyl acrylate, hydroxyethyl acrylate or hydroxybutyl acrylate, hydroxyethyl methacrylate, diethylene glycol diacrylate and diethylene or triethylene glycol dimethacrylate.

However, the material according to the invention is not limited to the monomers cited in the foregoing, but other monomers obviously may be added to the mixture, examples being ethylene glycol dimethacrylate or glycerol dimethacrylate, which may be added in addition to the diethylene glycol diacrylate and diethylene or triethylene glycol dimethacrylate in order to adjust the cross-linking level.

In general, the monomers chosen preferably have a boiling temperature above 100° C. in order to avoid the problems of bubbles at the end of high-temperature polymerization, and a molar mass between 130 and 350 g/mol, making it possible to eliminate the residual non-polymerized monomers easily at the end of the polymerization reaction.

In order to make this account more complete, there will now be described an example of the method for obtaining an acrylic polymer material according to the invention starting from the preferred initial mixture detailed above.

To achieve the sought polymerization, all the different monomers necessary for the reaction are mixed together. Advantageously these monomers are soluble in one another, and simple agitation is sufficient to produce a homogeneous mixture thereof.

The initiator compound or compounds necessary for starting the polymerization reaction is or are then added to this mixture.

In the case of a peroxide, this is generally unstable and poorly soluble in the monomer mixture at room temperature. It is then preferable to dissolve it in a fraction of mixture previously heated to approximately 40° C., then to remix this fraction containing the initiator compound with the rest of the monomer mixture.

The transfer agent is also added to the mixture before or after the initiator compound.

The mixture obtained is stored in the refrigerator, shielded from light.

To achieve the polymerization, small quantities of this mixture are removed, placed in molds and heated to a temperature between 75° C. and 95° C.

The speed and effectiveness of polymerization depend on the chosen reaction temperature.

At 75° C., for example, the polymerization lasts approximately ten hours and the polymer obtained is of high quality with a small proportion of residual monomers, or in other words monomers that have not reacted. At 95° C., on the other hand, the polymerization lasts only one hour, but the proportion of residual polymers remains high.

If a second peroxide is used, the polymerization is terminated by a second step of heating at a higher temperature, preferably 15 to 20° C. above the first.

During the polymerization, the temperature of the whole must be monitored so as to be kept substantially constant. The calories released by the reaction, which is exothermic, must be removed, for example by air or liquid convection.

Once the reaction has been terminated, and after cooling, the polymer is released from the mold.

The molds are preferably chosen such that polymer blocks of cylindrical general shape with low height, of the "slug" or "puck" type, are obtained after release from the mold. Such a shape is perfectly adapted to subsequent machining of these polymer blocks with a view to obtaining intraocular lenses.

Of course, direct molding of intraocular lenses with a suitable mold is also possible.

The polymer blocks must then be purified in order to free them of unreacted monomers and residual products derived in particular from the synthesis of each of the monomers used.

For this purpose, the polymer blocks are placed under a non-oxidizing atmosphere, or in other words under a stream of non-oxidizing gas such as steam, argon or nitrogen, for example, at a temperature between 120° C. and 150° C. and a reduced pressure between 20 and 100 mbar.

The duration of this treatment is between 12 and 48 hours, depending on the chosen temperature.

With such a treatment, it is possible to evaporate up to 4 to 10% of extractable products.

The blocks of polymer material are then ready to be machined at a temperature below the glass transition temperature of the polymer, in order to produce intraocular lenses according to the invention.

In order to describe the invention in full, several examples of acrylic polymer materials according to the invention are detailed below. These materials were obtained by radical polymerization starting from the following initial mixtures: (The proportions are expressed in percent by weight.)

EXAMPLE 1

| MONOMERS: | |
|---|---|
| 2-phenoxyethyl acrylate | 78.4% |
| n-butyl acrylate | 13.1% |
| hydroxyethyl acrylate | 2.6% |
| hydroxyethyl methacrylate | 4.4% |
| diethylene glycol diacrylate | 0.5% |
| diethylene glycol dimethacrylate | 0.5% |
| ethylene glycol dimethacrylate | 0.5% |
| INITIATOR COMPOUND: | |
| lauroyl diperoxide | 0.5% |
| TRANSFER AGENT: | |
| butanethiol | 0.05% |

In this way, after polymerization at 85° C. for a duration of four hours, there is obtained an acrylic polymer material having a refractive index equal to 1.536 and a glass transition temperature substantially equal to −8.4° C.

EXAMPLE 2

| MONOMERS: | |
|---|---|
| 2-phenoxyethyl acrylate | 73.7% |
| n-butyl acrylate | 8.2% |
| hydroxyethyl acrylate | 12.2% |
| hydroxyethyl methacrylate | 4.1% |
| diethylene glycol diacrylate | 0.6% |
| diethylene glycol dimethacrylate | 0.6% |
| ethylene glycol dimethacrylate | 0.6% |
| INITIATOR COMPOUND: | |
| lauroyl diperoxide | 0.5% |
| TRANSFER AGENT: | |
| butanethiol | 0.05% |

In this way, after polymerization at 75° C. for a duration of nine hours, there is obtained an acrylic polymer material having a refractive index equal to 1.535 and a glass transition temperature substantially equal to −7.7° C.

EXAMPLE 3

| MONOMERS: | |
|---|---|
| 2-phenoxyethyl acrylate | 72.1% |
| n-butyl acrylate | 10.3% |
| hydroxyethyl acrylate | 10.3% |
| hydroxyethyl methacrylate | 5.2% |
| diethylene glycol diacrylate | 0.7% |
| diethylene glycol dimethacrylate | 0.7% |
| ethylene glycol dimethacrylate | 0.7% |
| INITIATOR COMPOUND: | |
| lauroyl diperoxide | 0.5% |
| TRANSFER AGENT: | |
| butanethiol | 0.05% |

In this way, after polymerization at 75° C. for a duration of nine hours, there is obtained an acrylic polymer material having a refractive index equal to approximately 1.532 and a glass transition temperature substantially equal to −7.6° C.

EXAMPLE 4

| MONOMERS: | |
|---|---|
| 2-ethoxyethyl methacrylate | 48% |
| butyl acrylate | 37% |
| hydroxyethyl methacrylate | 12% |
| ethylene glycol dimethacrylate | 1.9% |
| INITIATOR COMPOUND: | |
| fast peroxide | 0.5% |
| TRANSFER AGENT: | |
| butanethiol | 0.07% |

In this way, after polymerization, there is obtained an acrylic polymer material having a refractive index equal to approximately 1.478.

EXAMPLE 5

| MONOMERS: | |
|---|---|
| 2-phenoxyethyl acrylate | 81% |
| 4-hydroxybutyl acrylate | 14.43% |
| hydroxyethyl methacrylate | 2.5% |
| diethylene glycol diacrylate | 0.5% |
| diethylene glycol dimethacrylate | 1.2% |
| INITIATOR COMPOUND: | |
| fast peroxide | 0.1% |
| slow peroxide | 0.25% |
| TRANSFER AGENT: | |
| octanethiol | 0.02% |

In this way, after polymerization, there is obtained an acrylic polymer material having a refractive index equal to approximately 1.535.

Obviously the invention is not limited to the preferred embodiments described in the foregoing and shown in the different figures, since the person skilled in the art will be able to make numerous modifications thereto and to imagine other variants without going beyond either the scope or the context of the invention defined by the claims.

The invention claimed is:

1. A cross-linked, hydrophobic, acrylic polymer material, deformable at room temperature, wherein the material is a three-dimensional macromolecular network obtained by radical polymerization starting from a mixture of acrylic and methacrylic monomers, characterized in that the mixture comprises:
    cross-linking compounds wherein said cross-linking compounds act, during the polymerization, to form the three-dimensional network; and
    additionally at least a transfer agent that, when the polymerization occurs, interrupts locally the three-dimensional network formation to create dangling chains,
    wherein said mixture comprises at least the following monomers
    an arylalkoxy acrylate or an arylalkoxy methacrylate;
    an alkyl acrylate;
    a hydroxylated acrylate;
    a hydroxylated methacrylate;
    a diol diacrylate; and
    a diol dimethacrylate,
    and wherein said monomers are comprised in the following amounts:
    between 45 and 89% by weight of arylalkoxy acrylate or arylalkoxy methacrylate;
    between 5 and 20% by weight of alkyl acrylate;
    between 5 and 20% by weight of a mixture of hydroxylated acrylate and hydroxylated methacrylate;
    between 1 and 3% by weight of a mixture of diol diacrylate and diol dimethacrylate.

2. An acrylic polymer material according to claim 1, characterized in that the transfer agent is a thiol or a halogenated product.

3. An acrylic polymer material according to claim 2, characterized in that the transfer agent is a thiol containing four to seventeen carbon atoms or a chlorinated product.

4. An acrylic polymer material according to claim 1, characterized in that said mixture comprises between 0.03 and 0.1% by weight of transfer agent.

5. An acrylic polymer material according to claim 1, characterized in that said mixture additionally comprises at least one initiator compound.

6. An acrylic polymer material according to claim 5, characterized in that the initiator compound is an alkyl peroxide.

7. An acrylic polymer material according to claim 5, characterized in that the mixture comprises between 0.3 and 1% by weight of initiator compound.

8. An acrylic polymer material according to claim 1, characterized in that the arylalkoxy acrylate or the arylalkoxy methacrylate is a compound chosen from among 2-phenoxyethyl acrylate, 2-phenoxy-2-ethoxyethyl acrylate, 2-phenoxy-2-ethoxy-2-ethoxyethyl acrylate and its higher oligomers for the arylalkoxy acrylate and from among 2-phenoxyethyl methacrylate, 2-phenoxy-2-ethoxyethyl methacrylate, 2-phenoxy-2-ethoxy-2-ethoxyethyl methacrylate and its higher oligomers for the arylalkoxy methacrylate.

9. An acrylic polymer material according to claim 1, characterized in that the alkyl chain of the alkyl acrylate contains 4 to 6 carbon atoms.

10. An acrylic polymer material according to claim 1, characterized in that the hydroxylated acrylate is a dihydroxyalkyl or dihydroxy-ethoxyalkyl monoacrylate, wherein the alkyl chain of the glycol contains 2 to 6 carbon atoms; and in that the hydroxylated methacrylate is a dihydroxyalkyl or dihydroxy-ethoxyalkyl monomethacrylate, wherein the alkyl chain of the glycol contains 2 to 6 carbon atoms.

11. An acrylic polymer material according to claim 1, characterized in that the diol diacrylate is diethylene glycol diacrylate, triethylene glycol diacrylate or an alkyldiol diacrylate, wherein the alkyl chain contains 2 to 6 carbon atoms and in that the diol dimethacrylate is diethylene glycol dimethacrylate or an alkyldiol dimethacrylate, wherein the alkyl chain contains 2 to 6 carbon atoms.

12. An acrylic polymer material according to claim 1, characterized in that it is obtained by radical polymerization starting from a mixture comprising at least the following monomers:
 2-phenoxyethyl acrylate;
 butyl acrylate;
 hydroxyethyl acrylate or hydroxybutyl acrylate;
 hydroxyethyl methacrylate;
 diethylene glycol diacrylate;
 diethylene glycol dimethacrylate or triethylene glycol dimethacrylate.

13. An acrylic polymer material according to claim 12, characterized in that the mixture additionally contains ethylene glycol dimethacrylate or glycerol dimethacrylate.

14. An acrylic polymer material according to claim 1, characterized in that the relative proportion between the hydroxylated acrylate and the hydroxylated methacrylate and between the diol diacrylate and the diol dimethacrylate varies from 30 to 70% of the one relative to the other, for each pair.

15. An intraocular lens comprising the acrylic polymer material according to claim 1.

16. A method for manufacturing, by radical polymerization, a cross-linked, hydrophobic acrylic polymer material according to claim 1, wherein the method comprises the steps of:
 forming the mixture comprising acrylic and methacrylic monomers, cross-linking compounds, and at least a transfer agent; and
 polymerizing said mixture in order to obtain by polymerization a three-dimensional macromolecular network that locally comprises dangling chains.

* * * * *